US012702860B1

(12) United States Patent
Al-Momen et al.

(10) Patent No.: US 12,702,860 B1
(45) Date of Patent: Aug. 11, 2026

(54) COLOR THERAPY DEVICE

(71) Applicant: IMAM MOHAMMAD IBN SAUD ISLAMIC UNIVERSITY, Riyadh (SA)

(72) Inventors: Sawsan Abd-Al Kareem Al-Momen, Riyadh (SA); Yahya Mubarak Suleiman Katatbeh, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/438,919

(22) Filed: Jan. 2, 2026

(51) Int. Cl.
*A61N 5/06* (2006.01)
*A61M 21/00* (2006.01)

(52) U.S. Cl.
CPC ........... *A61N 5/0618* (2013.01); *A61M 21/00* (2013.01); *A61M 2021/0044* (2013.01); *A61N 2005/0663* (2013.01)

(58) Field of Classification Search
CPC ......... A61N 5/0618; A61N 2005/0663; A61M 21/00; A61M 2021/0044
See application file for complete search history.

(56) References Cited

U.S. PATENT DOCUMENTS

2008/0123332 A1* 5/2008 Searfoss ............... A61M 21/00 368/256
2010/0179469 A1* 7/2010 Hammond ........... A61N 5/0624 604/20

(Continued)

FOREIGN PATENT DOCUMENTS

CN 202198986 U 4/2012
CN 104077991 B * 3/2018
KR 10-2023-0135224 A 9/2023

OTHER PUBLICATIONS

Bodymaster Store. (Jun. 20, 2024). Amazon.com: Hott Portable CD player, Retro bluetooth 5.3 CD players for home,music player with HiFi speaker,4000mah recheageable/remote contro/RGB night light/sleep timer/U disk/micro SD/AUX desktop CD players: Electronics. HOTT Portable CD Player,Retro Bluetooth (Year: 2024).*

(Continued)

*Primary Examiner* — Alex M Valvis
*Assistant Examiner* — Julie Thi Tran
(74) *Attorney, Agent, or Firm* — Oblon, McClelland, Maier & Neustadt, L.L.P.

(57) ABSTRACT

A color therapy device and a method of treating a patient's mental health. The color therapy device includes a control panel, a light sensor, an integrated timer, an ergonomic base, an integrated cooling system, an overhead adjustable light emitter, and a supplementary light emitter. The light sensor, the integrated timer, the integrated cooling system, the overhead adjustable light emitter, and the supplementary light emitter are all electronically connected to the control panel. The control panel is a rectangular prism and includes a touch screen and an additional light emitter, which is semicircular in shape. The cooling system prevents the color therapy device from overheating. The integrated timer turns off the color therapy device after a set time has elapsed, and the touch screen controls the color and intensity of the light emitted from each of the overhead adjustable light emitter and the supplementary light emitter.

15 Claims, 8 Drawing Sheets

(56) References Cited

U.S. PATENT DOCUMENTS

| | | | | |
|---|---|---|---|---|
| 2010/0277316 | A1* | 11/2010 | Schlangen | F21S 10/02<br>315/312 |
| 2013/0223073 | A1* | 8/2013 | Hayashi | F21V 21/00<br>362/249.02 |
| 2016/0323981 | A1* | 11/2016 | Clark | F21V 23/04 |
| 2020/0160798 | A1* | 5/2020 | Taekema | G03B 29/00 |
| 2023/0012300 | A1* | 1/2023 | Belkowski | H05B 47/165 |
| 2023/0372192 | A1* | 11/2023 | Ekhomu | A61H 23/02 |
| 2023/0414962 | A1 | 12/2023 | Sawyer | |

OTHER PUBLICATIONS

Legrand, "Whole House Lighting Controller" User Guide, LC7001, 2017, 30 pages.

Weiming Song, et al., "A Systematic Review of Light Therapy on Mental Health on and Beyond Earth", Psychology and Behavioral Sciences 2024, vol. 13, No. 3, Jul. 9, 2024, pp. 75-87.

* cited by examiner

COLOR THERAPY DEVICE

BACKGROUND

Technical Field

The present disclosure is directed to a therapy device, and more particularly relates to a color therapy device for treating mental health of patients.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Mental health disorders such as anxiety, depression, and bipolar disorder constitute a significant global public health challenge. These health conditions are characterized by complex multifactorial etiologies involving biological, psychological, and environmental factors that collectively impact individual well-being.

Despite growing awareness and increasing treatment demand, mental health care continues to face challenges. The limited availability of qualified professionals and the high cost of healthcare prevent millions from receiving timely and effective treatment.

Current treatment methods primarily rely on pharmacotherapy and evidence-based psychotherapies such as cognitive behavioral therapy (CBT), dialectical behavior therapy, and psychodynamic approaches. While these interventions remain fundamental to clinical practice and provide substantial benefit to many patients, they exhibit important limitations, including a narrow focus on specific symptom domains and limited integration of multisensory components.

Recent advances in mental health treatment, including digital therapeutics, psychedelic-assisted therapy, novel pharmacological agents, transcranial magnetic stimulation, and trauma-informed care, demonstrate the evolution of the field toward more comprehensive and personalized approaches. However, these inventions have yet to fully address the gap between treatment availability and patient need.

One reported system is a light therapy system that includes a remote-control device and at least one light therapy device. Each light therapy device includes a main body, a plurality of optical emitters, a system controller, and an onboard user interface device. The light therapy devices operate in a standalone mode using the onboard interface device and a cumulative mode where operating instructions are received from the remote-control device. However, this invention does not include a color therapy device for the treatment of the mental health of patients.

Another system is a full-color light wave bathroom that includes a light wave bathing house main part, that is equipped with a far infrared emitter in the light wave bathing house main part. A main control system is connected to far infrared emitter control end.is equipped with a colored physiotherapy device in the light wave bathing house main part. The colored physiotherapy device includes colored banks, light intensity control module. The colored banks include red color lamp, green color lamp, blue color lamp. The light intensity control module is connected respectively to the control end of red color lamp, green color lamp, blue color lamp, and the light intensity control module connects main control system. However, this system does not include a color therapy device for the treatment of the mental health of patients.

Each of the aforementioned inventions suffers from one or more drawbacks hindering their adoption, such as the non-inclusion of environmental and sensory modulator factors, lack of patient-centered care, insufficient non-pharmacological options, and absence of standardized sensory-environment protocols. Accordingly, it is one object of the present disclosure to address these deficiencies by providing a color therapy device that applies color therapy within a structured therapeutic framework. The present invention aims to provide a comprehensive, accessible, and effective solution for improving mental health and well-being through controlled sensory modulation.

SUMMARY

In an exemplary embodiment, a color therapy device is described. The color therapy device includes a control panel, a light sensor, an integrated timer, an ergonomic base, an integrated cooling system, an overhead adjustable light emitter, and a supplementary light emitter. The light sensor, the integrated timer, the integrated cooling system, the overhead adjustable light emitter, and the supplementary light emitter are electronically connected to the touch control panel. The control panel is a rectangular prism with a width of Z, a length of 0.8Z-1.2Z, and a height of 0.05Z-0.2Z. The control panel includes a touch screen and an additional light emitter shaped in a semicircle. The integrated cooling system prevents the color therapy device from overheating. The overhead adjustable light emitter is a circular unit, with a diameter X, with a central circular light in the center of the circular unit and a plurality of additional circular lights arranged within the perimeter of the circular unit, and emits a range of colors and has adjustable brightness. The supplementary light emitter is a cylindrical unit, having a first circular plane face, with a diameter Y, that forms a base of the supplementary light emitter, a second circular plane face that has a circular light in the center, and a curved face of the cylindrical unit has a plurality of circular lights arranged in straight horizontal lines. The overhead adjustable light emitter and the supplementary light emitter each emit independently adjustable wavelengths of light. The integrated timer is configured to turn off the color therapy device after a set time has elapsed. The touch control panel is configured to control the color and an intensity of the light emitted from each of the overhead adjustable light emitter and the supplementary light emitter.

In some embodiments, X=1-3 meters.

In some embodiments, the central circular light of the overhead adjustable light emitter has a diameter of 0.1X-0.3X.

In some embodiments, the plurality of additional circular lights of the overhead adjustable light emitter have a diameter of 0.05X-0.2X.

In some embodiments, Y=0.1-1.5 meters.

In some embodiments, the supplementary light emitter has a height of 0.5Y-1.0Y.

In some embodiments, the circular light in the center of the second circular plane face of the supplementary light emitter has a diameter of 0.5Y-0.9Y.

In some embodiments, the plurality of circular lights on the curved face of the supplementary light emitter have a diameter of 0.05Y-0.2Y.

In some embodiments, the overhead adjustable light emitters are configured to emit a color selected from the group consisting of blue, green, yellow, and pink.

In some embodiments, Z=10-100 centimeters.

In some embodiments, the additional light emitter shaped in a semicircle has a radius of 0.3Z-0.6Z.

In some embodiments, the touch screen has a length of 0.25Z-0.6Z and a width of 0.1Z-0.2Z.

In another exemplary embodiment, a method of treating a patient's mental health is described. The method includes assessing the patient's condition. The method further includes exposing the patient to light emitted from the color therapy device. A source of the light and the intensity of the light are based on the patient's condition.

In some embodiments, a patient is exposed to blue light if the patient is anxious or stressed, exposed to green light if the patient needs relaxation, exposed to yellow light if the patient needs energy, and exposed to pink light if the patient is depressed.

In some embodiments, the patient is exposed to the emitted light for 30-90 minutes.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
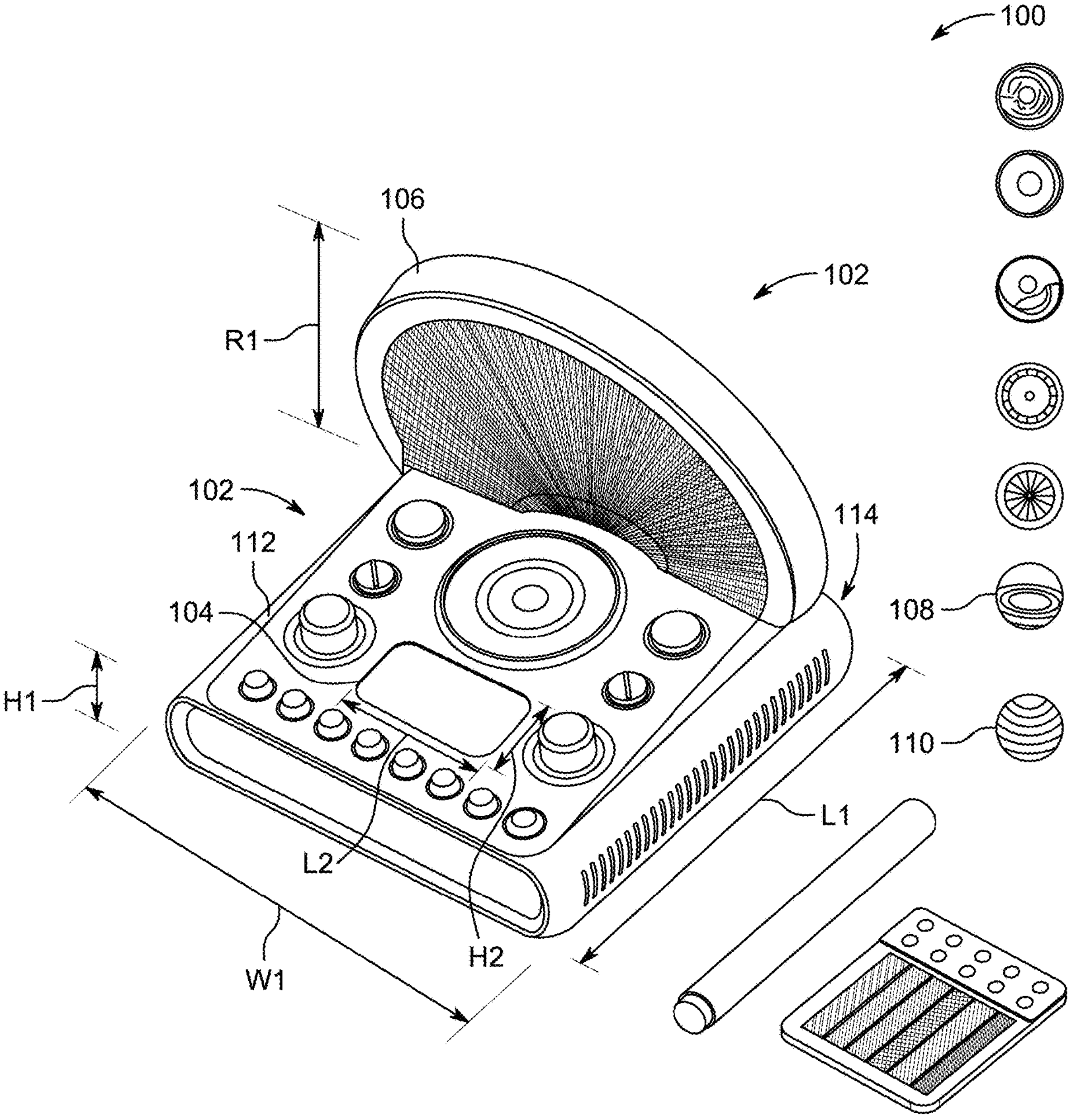
FIG. 1 is a perspective view of a color therapy device, according to certain embodiments.

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

Aspects of this disclosure are directed toward a color therapy device for treating mental health disorders. The color therapy device includes multiple interconnected components designed to address the need for an accessible, non-invasive, and cost-effective mental health treatment. By leveraging the therapeutic potential of specific color wavelengths and light exposure, the color therapy device provides a holistic and personalized approach that targets both psychological and sensory aspects of mental well-being in individuals. The color therapy device provides several advantages over conventional treatments, including but not limited to enhanced patient compliance through non-pharmacological intervention, reduced treatment costs, improved accessibility for diverse populations, and the ability to function as either a standalone therapeutic modality or as an adjunctive treatment complementing existing mental health care protocols.

Referring to FIG. 1A, a perspective view of a color therapy device 100 showing a control panel 102 is illustrated, according to certain embodiments. The color therapy device 100 is a apparatus designed to emit specific wavelengths of colored light to facilitate chromotherapy, a therapeutic use of color. The color therapy device 100 may be used to expose patients to targeted colors, often through Light Emitting Diode (LEDs) or filtered light sources to influence psychological well-being. The color therapy device 100 may also be used for stress reduction, mood enhancement, alleviation of insomnia, support in the management of certain skin conditions, and adjunctive treatment for seasonal affective disorder (SAD). The color therapy device 100 may be configurable for intensity and color selection, allowing for tailored sessions according to individual therapeutic needs.

The color therapy device 100 includes the control panel 102, which serves as the primary control structure of the color therapy device 100. The control panel 102 is configured to regulate operational parameters of the color therapy device 100. In one embodiment, the control panel 102 may include a microprocessor or a central processing unit (CPU) configured to execute control algorithms and process input data to enable precise and automated adjustment of therapeutic light output according to the needs of the patient. The control panel 102 is a rectangular prism with a width 'W1' of Z, a length 'L1' in a range of 0.8Z to 1.2Z, and a height 'H1' in a range of 0.05Z to 0.2Z for housing electronic components of the color therapy device 100. The rectangular prism configuration provides structural rigidity and efficient space utilization within the overall architecture of the control panel 102. In an embodiment, the control panel 102 may be fabricated from materials including, but not limited to, acrylonitrile butadiene styrene (ABS) plastic, polycarbonate, or composite materials providing durability and electromagnetic shielding properties.

The control panel 102 includes a touch screen 104. The touch screen 104 is configured to enable clinician selection of desired color wavelengths and light intensity parameters for therapeutic application. The touch screen 104 has a length 'L2' in a range of 0.25Z to 0.6Z and a width 'H2' in a range of 0.1Z to 0.2Z. In one embodiment, the touch screen 104 may be a liquid crystal display (LCD) or organic light-emitting diode (OLED) panel, responsive to tactile input from the finger of user or via a stylus. The touch screen 104 provides customizable settings, including but not limited to, discrete color selection from a predetermined spectrum, gradient color transitions with multiple wavelengths displayed sequentially or simultaneously, and adjustable duration of the treatment of the patients.

The control panel 102 further includes an additional light emitter 106 shaped in a semicircle. The additional light emitter 106 is semicircle shaped having a radius 'R1' in a range of 0.3Z to 0.6Z. The additional light emitter 106 may provide operational status indication, supplementary localized chromotherapy, visual treatment progress feedback, or ambient mood lighting synchronized with primary treatment protocols. The additional light emitter 106 includes light-emitting diodes (LEDs) emitting wavelengths in visible spectrum of light between 400 to 700 nm, which may be controlled independently.

In an embodiment, the measurements of the control panel 102, the touch screen 104, and the additional light emitter 106 are defined in terms of Z. According to the embodiments of the present disclosure, Z is in a range of 10 to 100 cm.

The color therapy device 100 further includes a light sensor 108. The light sensor 108 is electronically coupled to the control panel 102. The light sensor 108 may be configured to measure ambient lighting conditions within the treatment environment of the color therapy device 100. In one embodiment, the light sensor 108 may be a photodiode, phototransistor, or photoresistor responsive to the visible light wavelengths. The light sensor 108 transmits ambient light data to the control panel 102, which executes algorithms to automatically adjust emitted light intensity in real-time, enhancing therapeutic efficacy. The control panel 102 further ensures patient visual comfort and prevents excessive brightness exposure that may cause discomfort or photosensitivity reactions.

The color therapy device 100 further includes an integrated timer 110. The integrated timer 110 is electronically coupled to the control panel 102 and is configured to turn off the color therapy device 100 after a set time has elapsed. In one embodiment, the integrated timer 110 may be a microcontroller-based timing circuit capable of tracking elapsed treatment duration with high accuracy. In an exemplary embodiment, the integrated timer 110 receives user-defined time parameters from the touch screen 104, which may range from about 1 minute to about 180 minutes, and initiates a countdown sequence. Upon reaching zero elapsed time, the integrated timer 110 transmits a deactivation signal to the control panel 102 to terminate therapeutic light emission. The integrated timer 110 prevents overexposure to colored light, contributing to user safety.

The color therapy device 100 further includes an ergonomic base 112 specifically designed to enhance stability and user comfort during operation. The ergonomic base 112 allows the color therapy device 100 to be securely positioned on various surfaces, reducing the risk of accidental movement or tipping. In one embodiment, the ergonomic base 112 may be manufactured of non-slip materials to ensure a firm footing and facilitate safe, repeated use in diverse environments.

The color therapy device 100 further includes an integrated cooling system 114. The integrated cooling system 114 is electronically coupled to the control panel 102. The integrated cooling system 114 is configured to prevent the color therapy device 100 from overheating. The integrated cooling system 114 maintains a preset internal temperature by efficiently dissipating heat generated by the color therapy device 100. The integrated cooling system 114 further contributes to user safety and comfort, allowing for extended therapy sessions without interruption due to heat buildup.

Figure 2A:
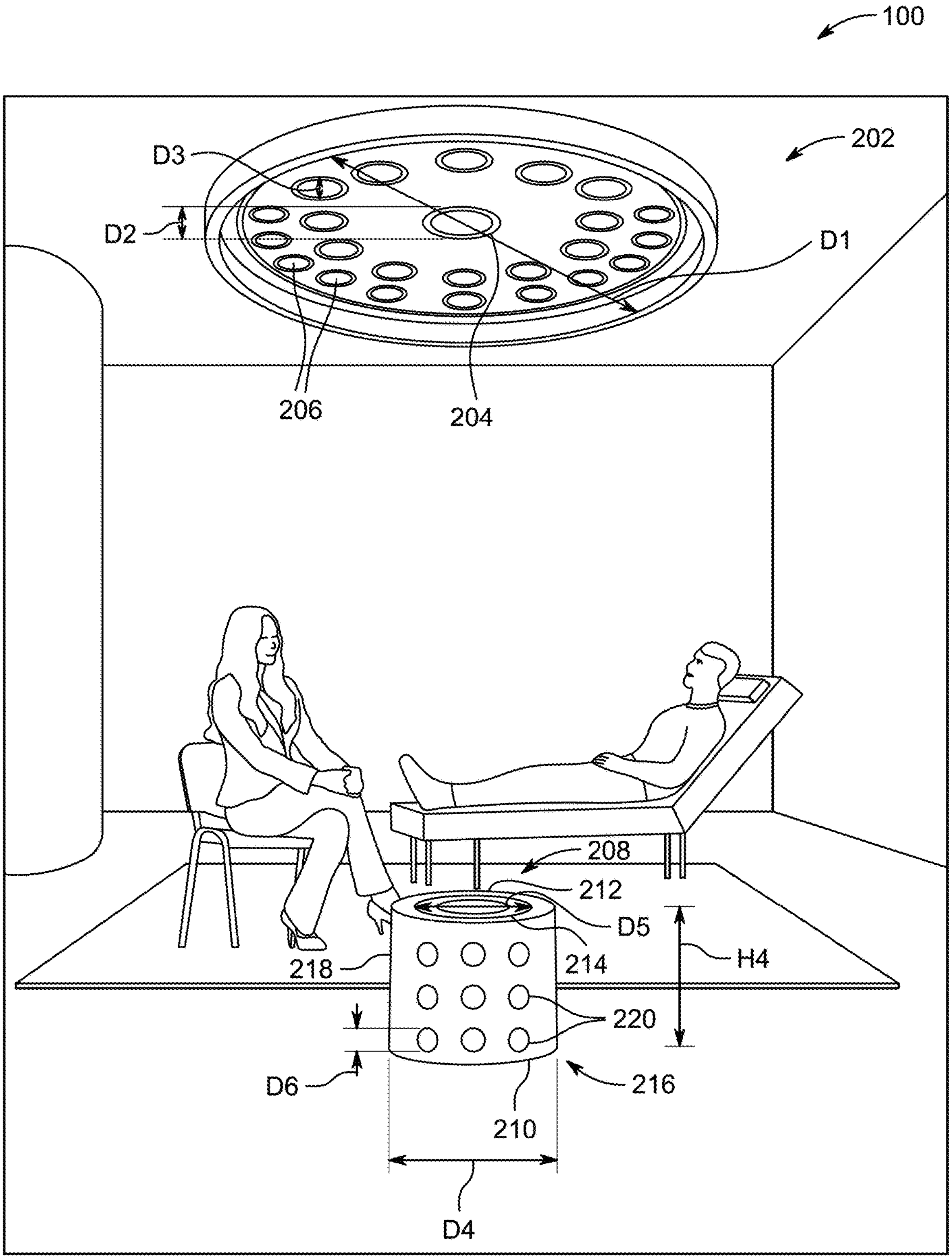
FIG. 2A is a schematic diagram showing an overhead adjustable light emitter and a supplementary light emitter used while treating a patient, according to certain embodiments.

Referring to FIG. 2A, a perspective view of the color therapy device 100 showing an overhead adjustable light emitter 202, and a supplementary light emitter 208 is illustrated, according to certain embodiments. The overhead adjustable light emitter 202 is electronically connected to the control panel 102. The overhead adjustable light emitter 202 is configured to emit therapeutic light wavelengths directed towards a patient positioned below the overhead adjustable light emitter 202. The overhead adjustable light emitter 202 is configured to emit a color selected from the group including blue, green, yellow, and pink.

In one embodiment, blue color light is used for calming anxious or stressed patients, green color light is used to provide relaxation for the patient, yellow color light is used if the patient needs energy, and pink color light is administered when the patient is experiencing depression.

In one embodiment, the overhead adjustable light emitter 202 is a circular unit, with a diameter 'D1' equal to X. The adjustable configuration of the overhead adjustable light emitter 202 enables clinicians to modify the position and angle of the overhead adjustable light emitter 202 for sufficient exposure and comfort during therapy sessions.

The overhead adjustable light emitter 202 includes a central circular light 204 located in the center of the circular unit. The central circular light 204 has a diameter 'D2' in a range of 0.1X to 0.3X. The central circular light 204 may function as a primary therapeutic light source, emitting uniform illumination across the visible wavelengths of the lights. The concentric positioning ensures symmetrical light distribution and focused therapeutic delivery directly to the target treatment area.

The overhead adjustable light emitter 202 further includes a plurality of additional circular lights 206 arranged within a perimeter of the circular unit. The plurality of additional circular lights 206 emit a range of colors and have adjustable brightness. The plurality of additional circular lights 206 has a diameter 'D3' in a range of 0.05X to 0.2X.

In an embodiment, the measurements of the overhead adjustable light emitter 202, the central circular light 204, and the plurality of additional circular lights 206 are defined in terms of X. According to the embodiments of the present disclosure, X is in a range of 1 to 3 m.

The color therapy device 100 further includes the supplementary light emitter 208. The supplementary light emitter 208 is electronically connected to the control panel 102. The supplementary light emitter 208 may be configured to provide auxiliary chromotherapy illumination along with the overhead adjustable light emitter 202. The supplementary light emitter 208 has a height 'H4' in a range of 0.5Y to 1.0Y.

In one embodiment, the supplementary light emitter 208 includes light-emitting diodes (LEDs) capable of emitting wavelengths within the visible range, controlled independently or synchronously with the primary light sources. The supplementary light emitter 208 may be positioned at peripheral locations surrounding the treatment area, enhancing overall light exposure coverage, intensifying therapeutic effects, or targeting specific anatomical regions needing localized chromotherapy intervention.

In one embodiment, the supplementary light emitter 208 is a cylindrical unit, having a first circular plane face 210, with a diameter 'D4' corresponding to Y. The first circular plane face 210 forms a base 216 of the supplementary light emitter 208. The base 216 provides structural support and facilitates stable positioning on horizontal surfaces or mounting to vertical structures. The cylindrical configuration provides efficient space utilization.

The base 216 may be manufactured using non-slip materials, including but not limited to rubber, silicone, or textured polymers to prevent unintended movement during operation, and may further include mounting apertures or adhesive surfaces for semi-permanent or permanent installation configurations.

The supplementary light emitter 208 further has a second circular plane face 212 that has a circular light 214 in the center. The circular light 214 has a diameter 'D5' in a range of 0.5Y to 0.9Y.

In one embodiment, a curved face 218 of the cylindrical unit has a plurality of circular lights 220 arranged in straight horizontal lines. The plurality of circular lights 220 on the curved face 218 of the supplementary light emitter 208 has a diameter 'D6' in a range of 0.05Y-0.2Y. In an embodiment, the measurements of the first circular plane face 210, the supplementary light emitter 208, the plurality of circular lights 220 on the curved face 218, and the second circular plane face 212 are defined in terms of Y. According to the embodiments of the present disclosure, Y is in a range of 0.1-1.5 m.

Figure 2B:
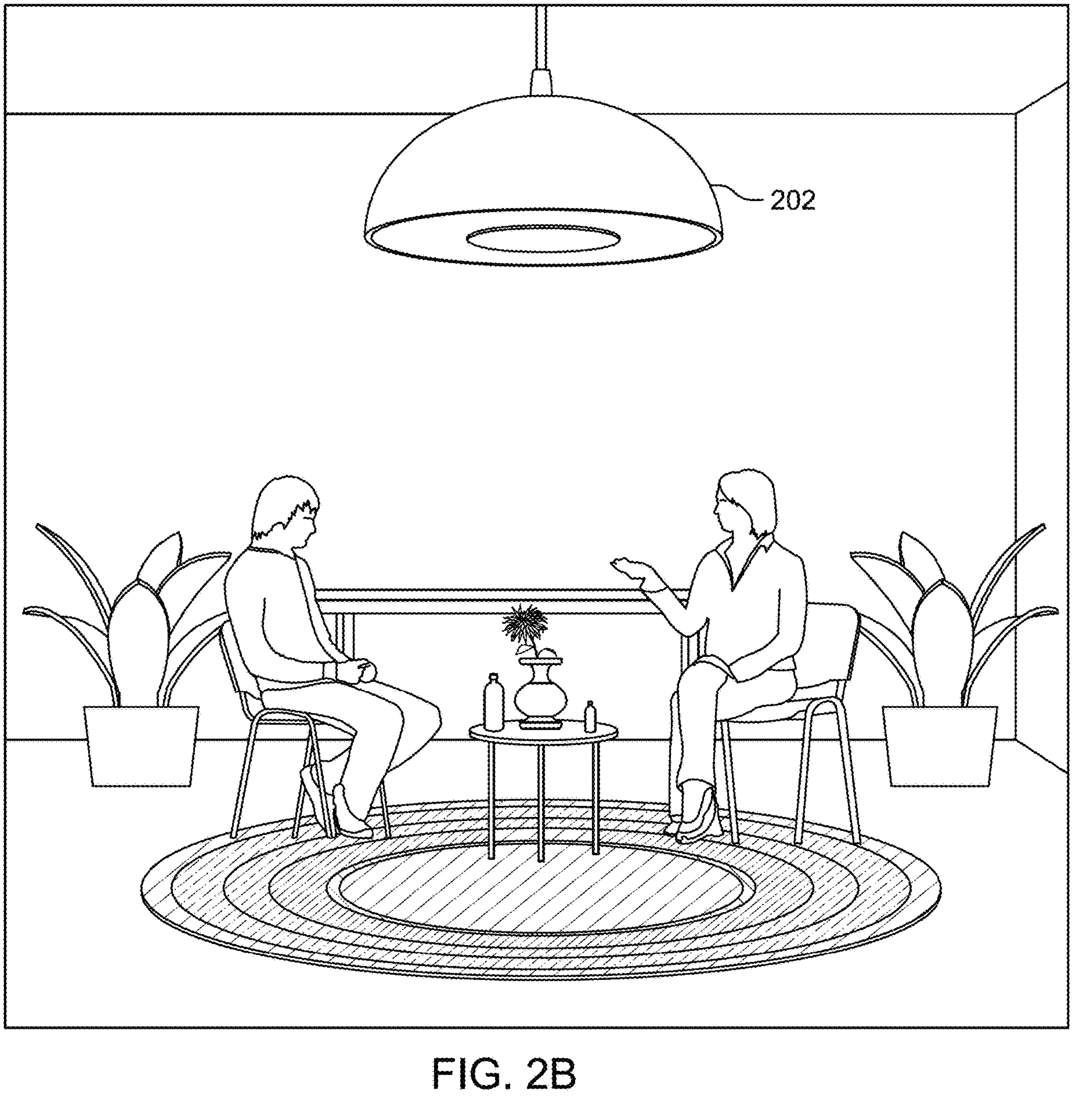
FIG. 2B is a schematic diagram showing the overhead adjustable light emitter being used while treating the patient, according to certain embodiments.

Referring to FIG. 2B, a schematic diagram showing the overhead adjustable light emitter 202 being used while treating the patient is illustrated, according to certain embodiments. The overhead adjustable light emitter 202 is positioned above the patient. The overhead adjustable light emitter 202 emits therapeutic wavelengths toward the patient positioned below to deliver targeted chromotherapy based on the assessed mental health condition. The overhead adjustable light emitter 202 emits a color selected from the group including blue, green, yellow, and pink. The clinician adjusts the position and light of the overhead adjustable light emitter 202 for efficient light delivery and to accommodate varying patients during treatment sessions.

Figure 3:
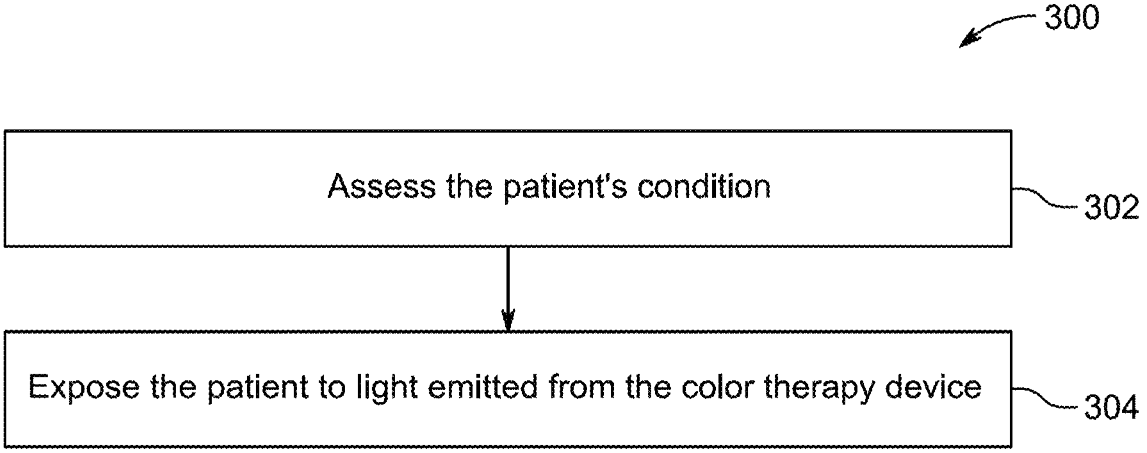
FIG. 3 is a flowchart of a method of treating a patient's mental health, according to certain embodiments.

Referring to FIG. 3, a flowchart of a method 300 of treating a patient's mental health is illustrated, according to certain embodiments. The method 300 includes a systematic sequence of steps executed using the color therapy device 100. Wavelengths in the visible range are utilized for the therapy. The method 300 may be implemented automatically through preprogrammed treatment protocols stored in the control panel 102, or manually initiated by a clinician or patient through user interface interactions, thereby providing flexible therapeutic intervention pathways.

The order in which the method 300 is described is not intended to be construed as a limitation, and any number of the described method steps can be combined in any order to implement the method 300. Additionally, individual steps may be removed or skipped from the method 300 without departing from the spirit and scope of the present disclosure.

At step 302, the method 300 includes assessing the condition of the patient. The method 300 involves a systematic evaluation of the mental health status of the patient, physiological responses, and therapeutic needs before initiating color therapy treatment. In one embodiment, the assessment may include administering standardized psychometric instruments, including but not limited to anxiety scales, depression inventories, or mood disorder assessments. The psychometric instruments may generate quantitative scores correlating with symptom severity, thereby enabling objective determination of the baseline mental health state of the patient.

The control panel 102 displays a digital assessment interface on the touch screen 104. The clinician inputs assessment data through interactive questionnaires, sliding scales, or multiple-choice selections. The control panel 102 may analyze the input data and compare patient responses against normative databases or diagnostic thresholds. Based on the assessment results, the color therapy device 100 categorizes the condition of the patient based on diagnostic classifications.

At step 304, the method 300 includes exposing the patient to light emitted from the color therapy device 100, wherein both the source of the light and the intensity of the light are based on the condition of the patient. After the assessment of the condition of patient, the control panel 102 automatically selects appropriate light emission parameters from stored treatment protocols corresponding to the diagnosed mental health condition of the patient.

In one embodiment, the overhead adjustable light emitter 202 may project therapeutic wavelengths downward toward the patient. The central circular light 204 emits a first wavelength selected from the visible spectrum between 400 nanometers to 700 nanometers.

The light sensor 108 continuously monitors ambient lighting conditions within the treatment space and transmits real-time illuminance data to the control panel 102. The control panel 102 dynamically adjusts the emitted light intensity from both the overhead adjustable light emitter 202 and supplementary light emitter 208, ensuring correct therapeutic dosage and prevents patient discomfort from excessive brightness.

The method 300 further includes exposing the patient to blue light when the patient is anxious or stressed, green light when relaxation is needed, yellow light when energy is needed, and pink light when the patient is depressed.

The method 300 further includes exposing the patient to the emitted light for 30 to 90 minutes. The integrated timer 110 tracks elapsed treatment duration according to protocols ranging from approximately 30 minutes to 90 minutes, depending on the needs of the patient.

In an exemplary embodiment, a patient assessed with anxiety disorders, the control panel 102 activates blue light emission at wavelengths with predefined intensity levels. The supplementary light emitter 208 simultaneously emits complementary wavelengths that match the blue light to enhance ambient therapeutic coverage. The plurality of circular lights 220 may activate in synchronized patterns, creating immersive chromotherapy environments that surround the patient with uniform color exposure.

The patient is exposed to green light if relaxation is needed, exposed to yellow light if the patient needs energy, and to pink light if the patient is depressed.

Specifically, when the patient needs relaxation or stress reduction, the method includes exposing the patient to green light. When the patient exhibits symptoms of fatigue or low energy, yellow light exposure is administered to stimulate alertness and improve mood. In cases where the patient is diagnosed with depression or low affect, the method 300 involves exposing the patient to pink light to evoke a calming and uplifting emotional response.

Figure 4:
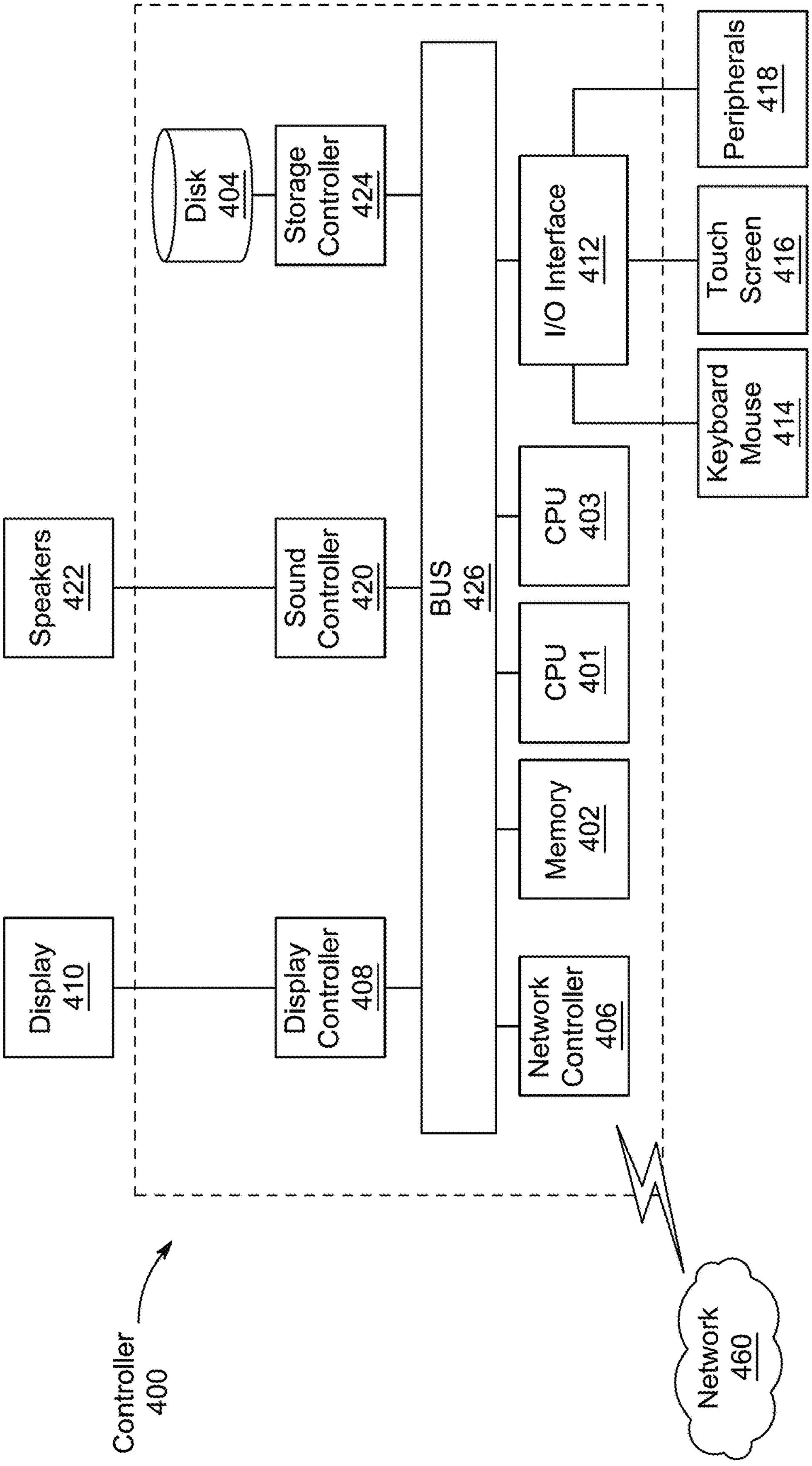
FIG. 4 is an illustration of a non-limiting example of details of computing hardware used in a control panel of the color therapy device, according to certain embodiments.

In FIG. 4, a controller 400 is described embodying the control panel 102 of the color therapy device 100 of the present disclosure, in which the controller 400 is a computing device which includes a CPU 401 which performs the processes described above/below. The process data and instructions may be stored in memory 402. These processes and instructions may also be stored on a storage medium disk 404 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 401, 403 and an operating system such as Microsoft Windows 7, Microsoft Windows 8, Microsoft Windows 10, UNIX, Solaris, LINUX, Apple MAC-OS and other systems known to those skilled in the art.

The hardware elements in order to achieve the computing device may be realized by various circuitry elements, known to those skilled in the art. For example, CPU 401 or CPU 403 may be a Xenon or Core processor from Intel of America or an Opteron processor from AMD of America, or may be other processor types that would be recognized by one of ordinary skill in the art. Alternatively, the CPU 401, 403 may be implemented on an FPGA, ASIC, PLD or using discrete logic circuits, as one of ordinary skill in the art would recognize. Further, CPU 401 and 403 may be implemented as multiple processors cooperatively working in parallel to perform the instructions of the inventive processes described above.

The computing hardware in FIG. 4 also includes a network controller 406, such as an Intel Ethernet PRO network interface card from Intel Corporation of America, for interfacing with network 460. As can be appreciated, the network 460 can be a public network, such as the Internet, or a private network such as an LAN or WAN network, or any combination thereof and can also include PSTN or ISDN sub-networks. The network 460 can also be wired, such as an Ethernet network, or can be wireless such as a cellular network including EDGE, 3G, 4G and 5G wireless cellular systems. The wireless network can also be Wi-Fi, Bluetooth, or any other wireless form of communication that is known.

The computing device further includes a display controller 408, such as a NVIDIA GeForce GTX or Quadro graphics adaptor from NVIDIA Corporation of America for interfacing with display 410, such as a Hewlett Packard HPL2445w LCD monitor. A general purpose I/O interface 412 interfaces with a keyboard and/or mouse 414 as well as a touch screen panel 416 on or separate from display 410. General purpose I/O interface also connects to a variety of peripherals 418 including printers and scanners, such as an OfficeJet or DeskJet from Hewlett Packard.

A sound controller 420 is also provided in the computing device such as Sound Blaster X-Fi Titanium from Creative, to interface with speakers/microphone 422 thereby providing sounds and/or music.

The general purpose storage controller 424 connects the storage medium disk 404 with communication bus 426, which may be an ISA, EISA, VESA, PCI, or similar, for interconnecting all of the components of the computing device. A description of the general features and functionality of the display 410, keyboard and/or mouse 414, as well as the display controller 408, storage controller 424, network controller 406, sound controller 420, and general purpose I/O interface 412 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 5.

Figure 5:
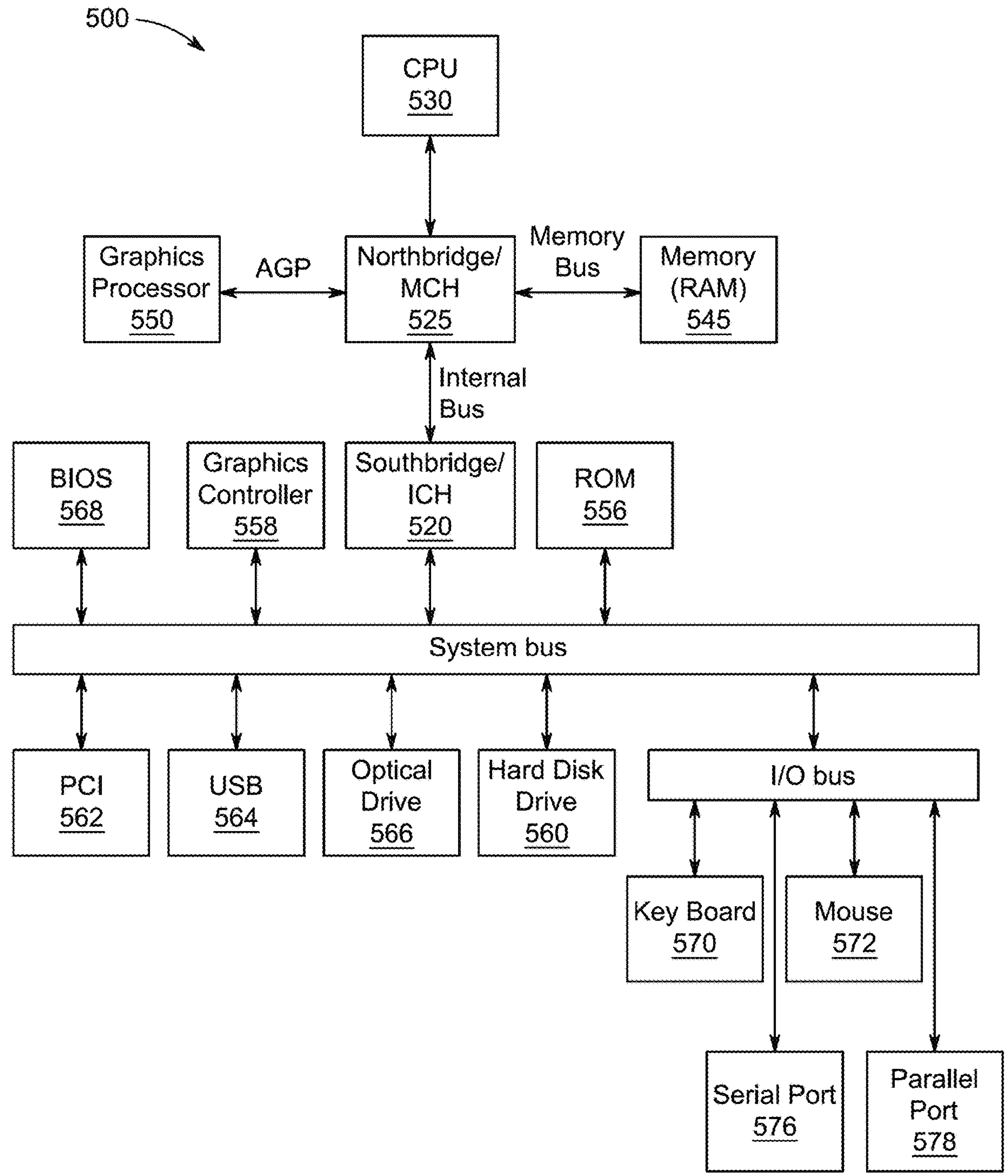
FIG. 5 is an exemplary schematic diagram of a data processing system used within the control panel of the color therapy device, according to certain embodiments.

FIG. 5 shows a schematic diagram of a data processing system used within the controlling module of the shaving device, according to certain embodiments, for performing the functions of the exemplary embodiments. The data processing system is an example of a computer in which code or instructions implementing the processes of the illustrative embodiments may be located.

In FIG. 5, data processing system 500 employs a hub architecture including a north bridge and memory controller hub (NB/MCH) 525 and a south bridge and input/output (I/O) controller hub (SB/ICH) 520. The central processing unit (CPU) 530 is connected to NB/MCH 525. The NB/MCH 525 also connects to the memory 545 via a memory bus, and connects to the graphics processor 550 via an accelerated graphics port (AGP). The NB/MCH 525 also connects to the SB/ICH 520 via an internal bus (e.g., a unified media interface or a direct media interface). The CPU Processing unit 530 may contain one or more processors and even may be implemented using one or more heterogeneous processor systems.

Figure 6:
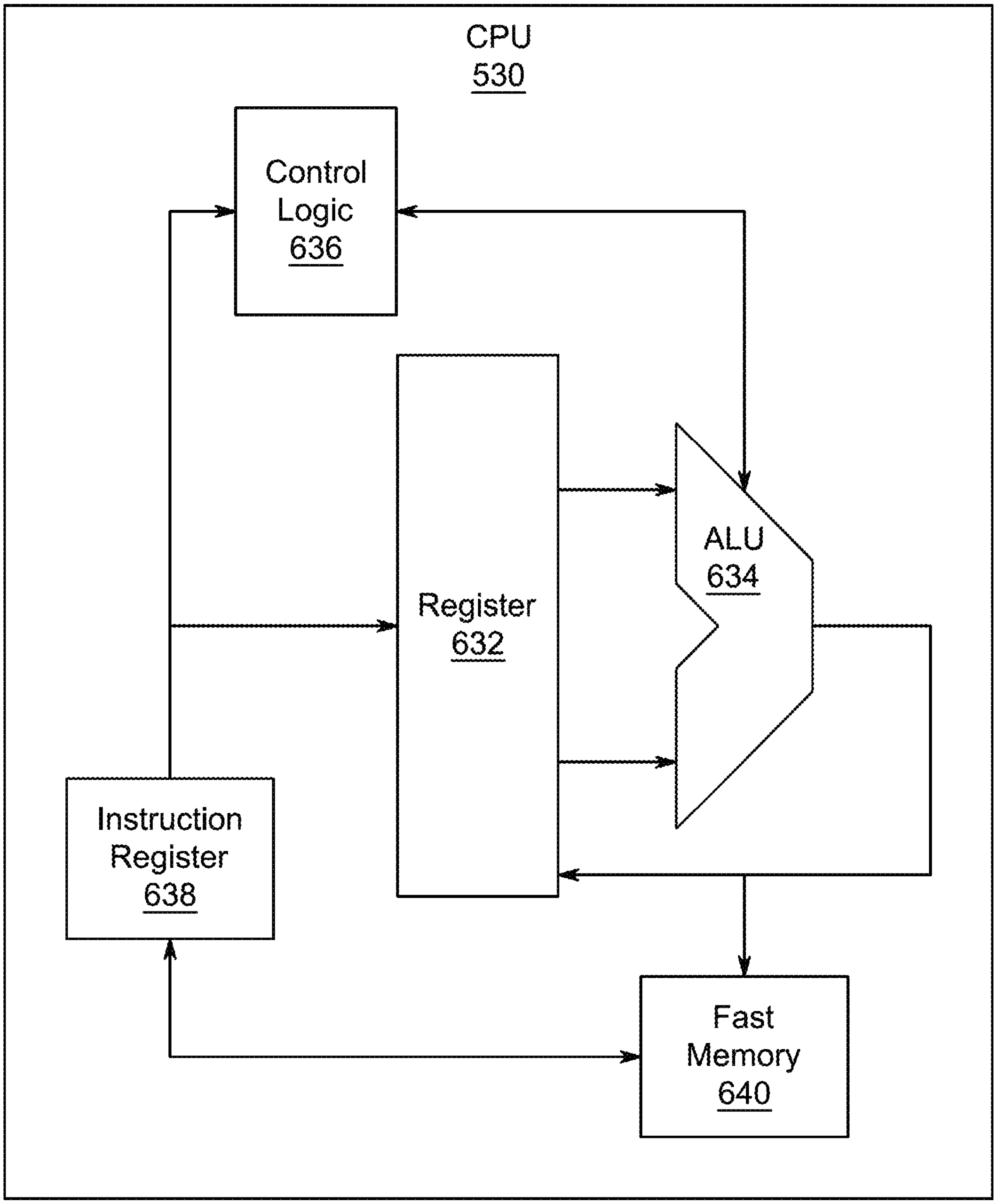
FIG. 6 is an exemplary schematic diagram of a processor used with the control panel, according to certain embodiments.

For example, FIG. 6 shows one implementation of CPU 530. In one implementation, the instruction register 638 retrieves instructions from the fast memory 640. At least part of these instructions are fetched from the instruction register 638 by the control logic 636 and interpreted according to the instruction set architecture of the CPU 530. Part of the instructions can also be directed to the register 632. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 634 that loads values from the register 632 and performs logical and mathematical operations on the loaded values according to the instructions. The results from these operations can be feedback into the register 632 and/or stored in the fast memory 640. According to certain implementations, the instruction set architecture of the CPU 530 can use a reduced instruction set architecture, a complex instruction set architecture, a vector processor architecture, and a very large instruction word architecture.

Furthermore, the CPU 530 can be based on the Von Neuman model or the Harvard model. The CPU 530 can be a digital signal processor, an FPGA, an ASIC, a PLA, a PLD, or a CPLD. Further, the CPU 530 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 5, the data processing system 500 can include that the SB/ICH 520 is coupled through a system bus to an I/O Bus, a read only memory (ROM) 556, universal serial bus (USB) port 564, a flash binary input/output system (BIOS) 568, and a graphics controller 558. PCI/PCIe devices can also be coupled to SB/ICH 588 through a PCI bus 562.

The PCI devices may include, for example, Ethernet adapters, add-in cards, and PC cards for notebook computers. The Hard disk drive 560 and CD-ROM 566 can use, for example, an integrated drive electronics (IDE) or serial advanced technology attachment (SATA) interface. In one implementation the I/O bus can include a super I/O (SIO) device.

Further, the hard disk drive (HDD) 560 and optical drive 566 can also be coupled to the SB/ICH 520 through a system bus. In one implementation, a keyboard 570, a mouse 572, a parallel port 578, and a serial port 576 can be connected to the system bus through the I/O bus. Other peripherals and devices that can be connected to the SB/ICH 520 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the needs of the intended back-up load to be powered.

Figure 7:
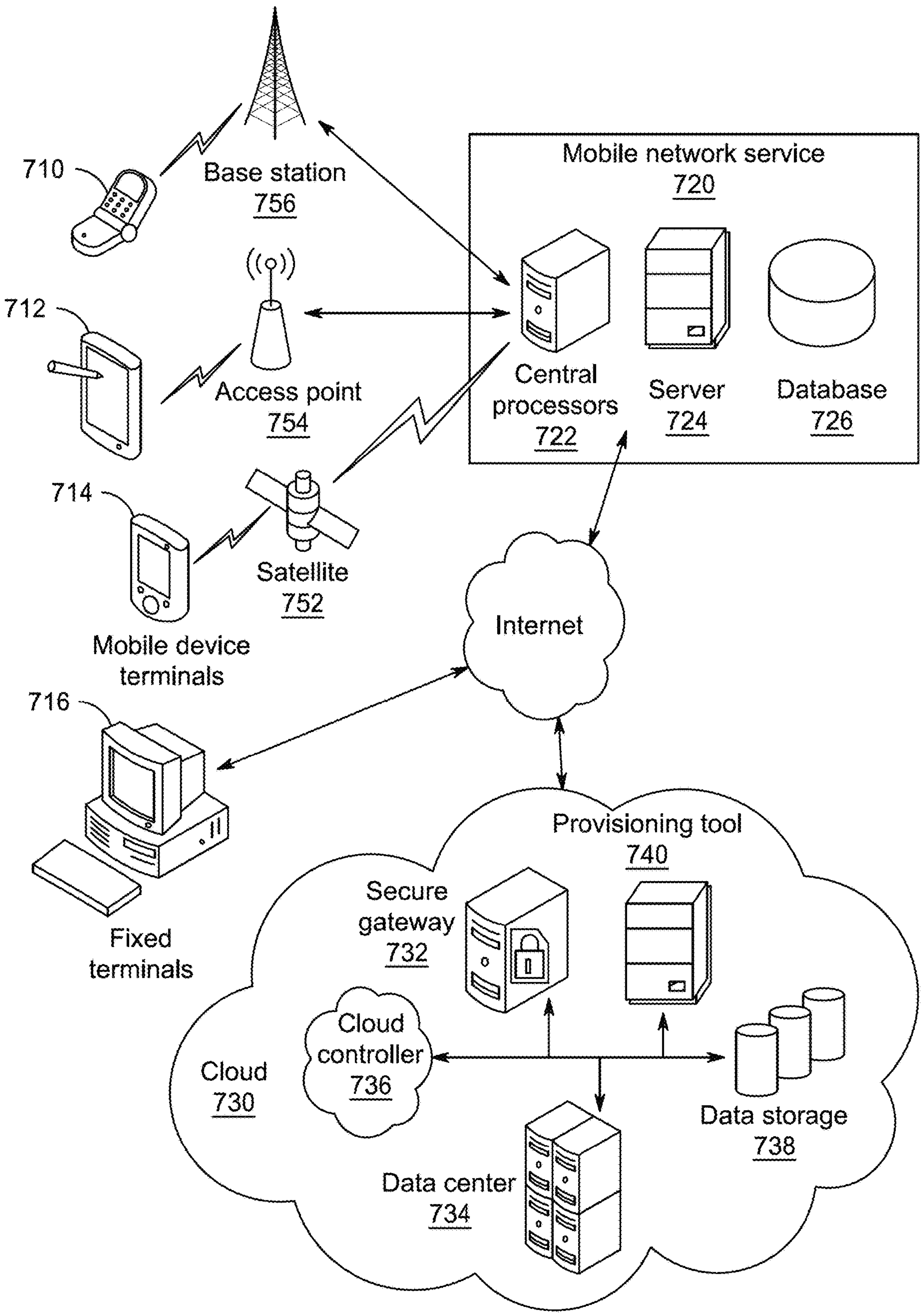
FIG. 7 is an illustration of a non-limiting example of distributed components which may share processing with a controller of the control panel, according to certain embodiments.

The functions and features described herein may also be executed by various distributed components of a system. For example, one or more processors may execute these system functions, wherein the processors are distributed across multiple components communicating in a network. The distributed components may include one or more client and server machines, such as cloud 730 including a cloud controller 736, a secure gateway 732, a data center 734, data storage 738 and a provisioning tool 740, and mobile network services 720 including central processors 722, a server 724 and a database 726, which may share processing, as shown by FIG. 7, in addition to various human interface and communication devices (e.g., display monitors 716, smart phones 710, tablets 712, personal digital assistants (PDAs) 714). The network may be a private network, such as a LAN, satellite 752 or WAN 754, or be a public network, may such as the Internet. Input to the system may be received via direct user input and received remotely in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A color therapy device, comprising:

a control panel, a light sensor, an integrated timer, an ergonomic base, an integrated cooling system, an overhead adjustable light emitter, and a supplementary light emitter, wherein the light sensor, the integrated timer, the integrated cooling system, the overhead adjustable light emitter and the supplementary light emitter are electronically connected to the control panel, wherein the control panel is a rectangular prism with a width of Z, a length of 0.8Z-1.2Z, and a height of 0.05Z-0.2Z, wherein the control panel includes a touch screen and an additional light emitter shaped in a semicircle, wherein the integrated cooling system prevents the color therapy device from overheating, wherein the overhead adjustable light emitter is a circular unit, with a diameter X, with a central circular light in the center of the circular unit and a plurality of additional circular lights arranged within the perimeter of the circular unit, and emits a range of colors and has adjustable brightness, wherein the supplementary light emitter is a cylindrical unit, having a first circular plane face, with a diameter Y, that forms a base of the supplementary light emitter, a second circular plane face that has a circular light in the center, and a curved face of the cylindrical unit has a plurality of circular lights arranged in straight horizontal lines, wherein the overhead adjustable light emitter and the supplementary light emitter each emit independently adjustable wavelengths of light, wherein the integrated timer is configured to turn off the color therapy device after a set time has elapsed, wherein the control panel is configured to control the color and an intensity of the light emitted from each of the overhead adjustable light emitter and the supplementary light emitter.

2. The color therapy device of claim 1, wherein X=1-3 meters.

3. The color therapy device of claim 1, wherein the central circular light of the overhead adjustable light emitter has a diameter of 0.1X-0.3X.

4. The color therapy device of claim 1, wherein the plurality of additional circular lights of the overhead adjustable light emitter have a diameter of 0.05X-0.2X.

5. The color therapy device of claim 1, wherein Y=0.1-1.5 meters.

6. The color therapy device of claim 1, wherein the supplementary light emitter has a height of 0.5Y-1.0Y.

7. The color therapy device of claim 1, wherein the circular light in the center of the second circular plane face of the supplementary light emitter has a diameter of 0.5Y-0.9Y.

8. The color therapy device of claim 1, wherein the plurality of lights on the curved face of the supplementary light emitter have a diameter of 0.05Y-0.2Y.

9. The color therapy device of claim 1, wherein the overhead adjustable light emitters are configured to emit a color selected from the group consisting of blue, green, yellow, and pink.

10. The color therapy device of claim 1, wherein Z=10-100 centimeters.

11. The color therapy device of claim 1, wherein the additional light emitter shaped in a semicircle has a radius of 0.3Z-0.6Z.

12. The color therapy device of claim 1, wherein the touch screen has a length of 0.25Z-0.6Z and a width of 0.1Z-0.2Z.

13. A method of treating a patient's mental health, comprising:

assessing the patient's condition; and exposing the patient to light emitted from the color therapy device of claim 1, wherein a source of the light and the intensity of the light are based on the patient's condition.

14. The method of claim 13, wherein the patient is exposed to blue light if the patient is anxious or stressed, exposed to green light if the patient needs relaxation, exposed to yellow light if the patient needs energy, and exposed to pink light if the patient is depressed.

15. The method of claim 13, wherein the patient is exposed to the emitted light for 30-90 minutes.

* * * * *